(12) United States Patent
Lawrence et al.

(10) Patent No.: US 7,094,430 B2
(45) Date of Patent: Aug. 22, 2006

(54) ANTIMICROBIAL SOLUTION FOR BOTH TROPICAL AND ORAL USE

(75) Inventors: Grady F. Lawrence, Salisbury, NC (US); W. Timothy Carlton, Salisbury, NC (US)

(73) Assignee: Innovative Healthcare Products, Inc., Huntsville, AL (US)

( * ) Notice: Subject to any disclaimer, the term of this patent is extended or adjusted under 35 U.S.C. 154(b) by 0 days.

(21) Appl. No.: 10/610,669

(22) Filed: Jul. 1, 2003

(65) Prior Publication Data

US 2004/0234463 A1 Nov. 25, 2004

Related U.S. Application Data

(60) Provisional application No. 60/430,208, filed on Dec. 2, 2002, provisional application No. 60/393,277, filed on Jul. 3, 2002.

(51) Int. Cl.
*A61K 33/40* (2006.01)
*A61K 7/08* (2006.01)
*A61K 7/75* (2006.01)

(52) U.S. Cl. .................. 424/615; 424/616; 424/70.22; 424/70.23; 424/70.24

(58) Field of Classification Search .............. 424/615, 424/616, 70.22, 70.23, 70.24
See application file for complete search history.

(56) References Cited

U.S. PATENT DOCUMENTS

| | | | | |
|---|---|---|---|---|
| 5,340,367 A | * | 8/1994 | Schultz et al. | 8/432 |
| 5,370,815 A | * | 12/1994 | Kessler | 510/131 |
| 5,645,428 A | * | 7/1997 | Yarborough | 433/215 |
| 5,863,521 A | * | 1/1999 | Schaefer et al. | 424/52 |
| 5,908,612 A | * | 6/1999 | Dailey et al. | 424/49 |
| 6,346,279 B1 | | 2/2002 | Rochon | |
| 6,723,714 B1 | | 4/2004 | Hanna | |

FOREIGN PATENT DOCUMENTS

| | | |
|---|---|---|
| EP | 0087049 | 2/1983 |
| EP | 0351772 | 7/1989 |
| EP | 0289463 | 5/1992 |
| EP | 0845526 | 6/1998 |
| GB | 2101350 | 1/1983 |
| WO | PCT WO 39/14183 | 7/1993 |
| WO | PCT WO 98/11777 | 3/1998 |
| WO | PCT WO 98/21305 | 5/1998 |

OTHER PUBLICATIONS

U.S. Department of Health and Human Services. *Oral Health In America: A Report of the Surgeon General —Executive Summary*. Rockville, MD: U.S. Department of Health and Human Services, National Institute of Dental and Craniofacial Research, National Institutes of Health, 2000.

* cited by examiner

*Primary Examiner*—Vickie Kim
(74) *Attorney, Agent, or Firm*—Lanier Ford Shaver & Payne P.C.

(57) ABSTRACT

An antimicrobial solution is provided for use in the cleaning of dentures and toothbrushes, as well as, for use as an oral mouthwash and/or a general disinfectant. The primary active ingredients of the present invention include an approximately 4.5% solution of hydrogen peroxide as an antibacterial agent and sodium lauryl sulfate as a cleansing agent. The present invention is mixed and maintained in liquid form. Additional ingredients are included to ensure the activation of the various antibacterial or cleansing agents. The present invention overcomes the problems with presently available denture cleansers because it does not require the use of hot, warm, or even cold water to activate the cleansing agent.

30 Claims, No Drawings

ANTIMICROBIAL SOLUTION FOR BOTH TROPICAL AND ORAL USE

REFERENCE TO RELATED APPLICATIONS

This application claims priority to Provisional Patent Application, U.S. Ser. No. 60/393,277, entitled "Method of Preserving Dentures as They are Cleaned and Antimicrobial Toothbrush Cleaner" filed Jul. 3, 2002, and Provisional Patent Application, U.S. Ser. No. 60/430,208, entitled "Oral Hygiene" filed Dec. 2, 2002, which are both fully incorporated herein by reference.

BACKGROUND OF THE INVENTION

This invention generally relates to an antibacterial solution for either oral or topical use. In particular, the present invention relates to an antimicrobial solution for internal use by an individual or as a cleaning agent. More particularly, the present invention relates to an antimicrobial solution for use in the cleaning of dentures and toothbrushes, as well as, for use as an oral mouthwash and/or a general disinfectant.

Oral hygiene has been shown to be closely associated with the general health of an individual. Opportunistic infections have been linked to microorganisms commonly found in the oral cavity. The mouth has been described as the primary portal of entry and site of disease for microbial infections that affect the general health. It is, therefore, desirable to provide an antimicrobial solution for use in combating the growth and spread of the microorganisms that are the primary cause of such infections for use both within the oral cavity and as a cleansing solution for devices used within the oral cavity, such as, but not limited to, toothbrushes and dentures.

Currently available denture cleansers are available in tablet format only and generally function to clean dentures without killing harmful bacteria. Their cleaning action is known as "effervescence" and this action has been shown to damage and even to destroy dentures over time as it slowly pits the exterior surface of the denture. Further, such tablet cleaners must be dissolved in warm or hot water. This higher temperature water has been known to warp dentures distorting their proper fit and ultimate damaging them beyond repair. It is, therefore, desirable to provide a liquid denture cleanser capable of cleaning dentures without damaging them and simultaneously killing harmful bacteria that may be growing thereon.

Toothbrushes have been shown to retain particles of food and other material removed from the teeth of a user during brushing even when thoroughly rinsed after use. As a result, a breeding ground for bacteria is created that is repeatedly placed in the mouth of a user exposing that person to numerous unknown microorganisms that are potential causes of various periodontal and other diseases. It is, therefore, desirable to provide a toothbrush cleanser that can either significantly reduce or eliminate harmful bacteria from a toothbrush between uses.

SUMMARY OF THE INVENTION

The present invention recognizes and addresses various of the foregoing limitations and drawbacks, and others, concerning the reduction and elimination of harmful microorganisms on devices used within the oral cavity of an individual, as well as within the oral cavity itself. Therefore, the present invention is directed to an antimicrobial solution for use in the cleaning of dentures and toothbrushes, as well as, for use as an oral mouthwash and/or a general disinfectant.

It is, therefor, a principle object of the subject invention to provide an antimicrobial solution suitable for internal use. More particularly, it is an object of the present invention to provide such a solution for use as a mouthwash. In such context, it is still a more particular object of the present invention to provide an antimicrobial solution whose primary active ingredients are hydrogen peroxide and sodium lauryl sulfate.

Further, it is a principle object of this invention to provide an antimicrobial solution suitable for use as a topical disinfectant. It is a further object of the present invention to provide such a solution that is capable of eliminating all staphylococcus bacteria on contact.

Still further, it is a principal object of the present invention to provide an antimicrobial solution suitable for use as a denture cleanser. It is a further object of the present invention to provide such a solution in a liquid form. In such context, it is still a more particular object of the present invention to provide an antimicrobial solution capable of cleaning dentures while significantly reducing the harmful bacteria that cause periodontal and other diseases thereon.

It is yet another principal object of the present invention to provide an antimicrobial solution suitable for use as a toothbrush cleanser. It is a further object of the present invention to provide such a solution where mere soaking of the toothbrush is sufficient for significant reduction or even elimination of growth of any bacteria thereon. In such context, it is a particular object of the present invention to provide an antimicrobial solution whose primary active ingredients are hydrogen peroxide and sodium lauryl sulfate.

Additional objects and advantages of the invention are set forth in, or will be apparent to those of ordinary skill in the art from, the detailed description as follows. Also, it should be further appreciated that modifications and variations to the specifically illustrated and discussed features and materials hereof may be practiced in various embodiments and uses of this invention without departing from the spirit and scope thereof, by virtue of present reference thereto. Such variations may include, but are not limited to, substitutions of the equivalent means, features, and materials for those shown or discussed, and the functional or positional reversal of various parts, features, or the like.

Still further, it is to be understood that different embodiments, as well as different presently preferred embodiments, of this invention, may include various combinations or configurations of presently disclosed features, elements, or their equivalents (including combinations of features or configurations thereof not expressly shown in the figures or stated in the detailed description).

These and other features, aspects and advantages of the present invention will become better understood with reference to the following descriptions and appended claims. The accompanying drawings, which are incorporated in and constitute a part of this specification, illustrate an embodiment of the invention and, together with the descriptions, serve to explain the principles of the invention.

In one exemplary embodiment, there may be provided an antimicrobial solution for aiding in the effort to gain or maintain oral hygiene. Such solution may comprise a combination of 4.5% hydrogen peroxide as a bactericide and sodium lauryl sulfate as a cleansing agent. Such solution may be provided in a liquid form.

The antimicrobial solution is intended for use as a topical and oral disinfectant/cleanser. To that end, it is envisioned that such solution may be used as both a toothbrush and a denture disinfectant/cleanser, wherein such toothbrush or denture may be soaked in the solution overnight and without the use of hot, warm, or cold water. During such treatment of the toothbrush or denture, the cleansing agent may thus act without effervescence—eliminating the primary cause of damage to dentures when using currently available cleansers. Further, during such overnight treatment of the toothbrush and dentures, elimination of substantially all harmful bacteria may be provided by the bactericide within the solution, thus reducing the likelihood of re-introducing harmful microorganisms into the oral cavity.

Further still, the antimicrobial solution is envisioned as a mouthwash and a topical disinfectant. In each case, the solution may be used by an individual to reduce or eliminate harmful bacteria. In the case of the solution's use as a mouthwash, the solution may be used to eliminate bacteria other than just those that may cause bad breath. Instead the solution of the present invention may be used to reduce or eliminate all harmful bacteria within the oral cavity. As a topical disinfectant, a user may clean surfaces such as those found in medical offices, hospitals or restaurants for the reduction or elimination of harmful bacteria.

DETAILED DESCRIPTION OF THE PREFERRED EMBODIMENTS

Reference will now be made in detail to presently preferred embodiments of the invention, examples of which are fully represented in the accompanying tables. Such examples are provided by way of an explanation of the invention, not limitation thereof. In fact, it will be apparent to those skilled in the art that various modifications and variations can be made in the present invention, without departing from the spirit and scope thereof. For instance, features illustrated or described as part of one embodiment can be used on another embodiment to yield a still further embodiment. Still further, variations in selection of materials and/or characteristics may be practiced, to satisfy particular desired user criteria. Thus, it is intended that the present invention cover such modifications and variations as come within the scope of the present features and their equivalents.

As disclosed above, the present invention is particularly concerned with an antimicrobial solution for use in the cleaning of dentures and toothbrushes, as well as, for use as an oral mouthwash and/or a general disinfectant. The solution of the present invention is comprised primarily of four main ingredients: water, hydrogen peroxide, phosphoric acid, and sodium lauryl sulfate. Colorings and/or flavorings may be used as desired to aid in establishing both a commercial differentiation of the present invention from any currently competitive products, as well as, to simple make the product more appealing to users.

A preferred formulation of the solution comprising the present invention is as follows:

| MAIN MIX | % BY WEIGHT |
| --- | --- |
| Water | 90.81% |
| 50% Hydrogen Peroxide | 9.00% |
| Phosphoric Acid | 0.04% |
| Sodium Lauryl Sulfate | 0.15% |
| FD&C Blue #1 | 0.00% |
| FD&C Yellow #5 | 0.00% |

The liquid ingredients are mixed at room temperature. The hydrogen peroxide serves as the primary antibacterial agent and the sodium lauryl sulfate as the primary cleansing agent. While the preferred formulation includes a solution of 4.5% hydrogen peroxide and 0.15% sodium lauryl sulfate, it should be generally known that such percentages are not exact and may be with a range of acceptable values. For example, the percentage of hydrogen peroxide may be from generally about 3% to generally about 5% (or generally about 6–10% by weight) of the present solution. Further, the percentage of sodium lauryl sulfate may be from generally about 0.10% to generally about 0.20% by weight.

The phosphoric acid in the solution merely serves as a reagent to cause the hydrogen peroxide to break down into the free radicals that are antibacterial. The quantity of phosphoric acid in the solution is intentionally maintained at a restricted amount (at least about 0.03% and not more than about 0.05%) to ensure the safety of the product for oral use. The strength of such bactericide, however, remains safe for use as a mouthwash or to clean dentures and toothbrushes while retaining its effectiveness in significantly reducing or eliminating harmful bacteria on contact.

A method for cleaning dentures with the present invention includes providing a container of suitable size to hold the dentures, placing the dentures into the container and providing enough of the present invention to cover the dentures in the container. The dentures should remain in the solution of the present invention for at least 15 minutes, more preferably, overnight, to be simultaneously cleaned and sanitized. The cleaned and sanitized dentures may then be removed from the container and brushed with a similarly cleaned and sanitized toothbrush and toothpaste. Following a rinsing with cold water the dentures are ready for use.

Similarly, a toothbrush may be cleaned and sanitized by submerging the bristle-end of the brush into the solution of the present invention for a period of time of at least fifteen minutes, more preferably, overnight. The cleansing action of the sodium lauryl sulfate will serve to loosen and remove any remaining food particles trapped within the bristles of the toothbrush. The activated hydrogen peroxide serves to reduce or eliminate all the harmful bacteria still on the surfaces of the toothbrush after its use.

The present invention similarly functions as a safe and effective mouthwash by placing a quantity of the solution into the oral cavity and swishing it around; without swallowing and spitting it out. The activated hydrogen peroxide serves to kill not just the bacteria that cause bad breath but substantially all harmful bacteria on contact. Such action reduces the risk of periodontal infection and other related diseases and conditions.

Finally, the present invention may be used as a topical cleanser and disinfectant for use in/on those areas requiring a higher than ordinary level of cleaning. Such locations include, but are limited to, hospitals, doctor's offices, restaurants, and bathrooms. The active ingredients of the solution of the present invention serve to clean these locations while simultaneously killing many of the harmful bacteria on contact.

EXAMPLES

Example 1

Three toothbrushes were submitted for testing in which one was used an unspecified amount of time prior to submission and the other two were unused. One of the unused toothbrushes was used immediately prior to performance of the testing of the solution of the present invention. The specimens were identified as:

1—The previously used brush;
2—The brush used just prior to testing; and
3—The unused brush.

Each brush was suspended in a growth medium and a sample of any bacterial growth was taken. Each brush was then suspended for 15 minutes in the present invention. Finally, each brush was suspended in a growth medium identical to the one used earlier and a second sample of any bacterial growth was taken for each brush. The six separate samples were incubated at 37 C for approximately 18 hours and examined for evidence of growth. The table below summarizes the findings of the bacterial colony counts.

TABLE 1

Toothbrush Cleansing Results

| Toothbrush Number | Before Treatment | After Treatment |
|---|---|---|
| 1 | 12,900 CFUs/ml | 100 CFUs/ml |
| 2 | 10,000 CFUs/ml | No Growth |
| 3 | No Growth | No Growth |

Example 2

The present invention was tested against a commercially available denture cleanser and a 3% solution of $H_2O_2$ to test its effectiveness to inhibit growth of ten various target microorganisms commonly found in the human mouth. Included among the microorganisms were *candida albicans, staphylococcus aureus, streptococcus sanguia*, and *fusobacterium nucleatum*. Three samples of each microorganism were prepared for introduction of one of the various treatments—either, the present invention, a commercially-available denture cleanser, or a 3% solution of $H_2O_2$. The table blow partailly summarizes the results in terms of the titration of zones (in millimeters) of inhibition of growth.

TABLE 2

Titration of Zones of Inhibition of Growth of Target Microorganisms

| Target Microorganism | Solution | St. | Dilution | | | | | | |
|---|---|---|---|---|---|---|---|---|---|
| | | | 1/2 | 1/4 | 1/8 | 1/16 | 1/32 | 1/64 | 1/128 |
| Candida albicans | *P.I. | 6.5 | **NI | NI | NI | NI | NI | NI | NI |
| | Cleanser | NI | NI | NI | NI | NI | NI | NI | NI |
| | $H_2O_2$ | 5.5 | 5.0 | NI | NI | NI | NI | NI | NI |
| Staphylococcus aureus | P.I. | 7.0 | 8.0 | 7.5 | 7.0 | NI | NI | NI | NI |
| | Cleanser | NI | NI | NI | NI | NI | NI | NI | NI |
| | $H_2O_2$ | 10.0 | 5.0 | NI | NI | NI | NI | NI | NI |
| Streptococcus sanguia | P.I. | 12.5 | 10.5 | 8.5 | 8.0 | 8.0 | 5.0 | 5.0 | NI |
| | Cleanser | NI | NI | NI | NI | NI | NI | NI | NI |
| | $H_2O_2$ | 10.0 | 6.5 | NI | NI | NI | NI | NI | NI |
| Fusobacterium nucleatum | P.I. | 15.0 | 13.5 | 8.5 | 8.0 | 5.0 | NI | NI | NI |
| | Cleanser | NI | NI | NI | NI | NI | NI | NI | NI |
| | $H_2O_2$ | 17.0 | 13.0 | 7.0 | 6.0 | NI | NI | NI | NI |

*P.I. = Present Invention;
**NI = No inhibition detected

Although a preferred embodiment and multiple examples of the present invention have been described using specific terms and devices, such description and examples are for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of various other embodiments may be interchanged both in whole or in part. Therefore, the spirit and scope of the appended claims should not be limited to the description of the preferred version contained herein.

What is claimed is:

1. An antimicrobial solution for topical and oral use consisting of:
   a) sodium lauryl sulfate as a cleansing agent;
   b) hydrogen peroxide as an antibacterial agent;
   c) phosphoric acid as a reagent for activating said antibacterial agent; and
   d) water.
2. The antimicrobial solution of claim 1, wherein said cleansing agent comprises about 0.10% to generally about 0.20% of said solution by weight.
3. The antimicrobial solution of claim 1, wherein said cleansing agent comprises about 0.15% of said solution by weight.
4. The antimicrobial solution of claim 1, wherein said antibacterial agent comprises about 6.0% to about 10% of said solution by weight.
5. The antimicrobial solution of claim 4, wherein said antibacterial agent comprises about 9.0% of said solution by weight.
6. The antimicrobial solution of claim 4, wherein said reagent causes said hydrogen peroxide to breakdown into free radicals which are antibacterial.
7. The antimicrobial solution of claim 6, wherein said reagent comprises about 0.04% of said solution by weight.
8. The antimicrobial solution of claim 1, wherein said reagent is comprises about 0.04% of said solution by weight.
9. The antimicrobial solution of claim 1, wherein said solution is a liquid denture cleanser.
10. The antimicrobial solution of claim 1, wherein said solution is a toothbrush cleanser.
11. The antimicrobial solution of claim 1, wherein said solution is a mouthwash.
12. The antimicrobial solution of claim 1, wherein said solution is a disinfectant.
13. An antimicrobial solution for topical oral use consisting of:
   a) sodium lauryl sulfate as a cleansing agent;
   b) hydrogen peroxide as a antibacterial agent;
   c) phosphoric acid as a reagent;
   d) water; and
   e) at least one coloring agent selected from the group consisting of FD&C blue#1 and FD&C Yellow #5.
14. The antimicrobial solution of claim 13, wherein said cleansing agent comprises about 0.10% to about 0.20% of said solution by weight.
15. The antimicrobial solution of claim 14, wherein said cleansing agent comprises about 0.15% of said solution by weight.
16. The antimicrobial solution of claim 13, wherein said antibacterial agent comprises about 6.0% to about 10% of said solution by weight.
17. The antimicrobial solution of claim 16, wherein said antibacterial agent comprises about 9.0% of said solution by weight.
18. The antimicrobial solution of claim 17, wherein said reagent causes said hydrogen peroxide to breakdown into free radicals which are antibacterial.
19. The antimicrobial solution of claim 13, wherein said reagent comprises about 0.04% of said solution by weight.

20. The antimicrobial solution of claim 13, wherein said water comprises greater than about 90% of said solution by weight.

21. The antimicrobial solution of claim 13, wherein said at least one coloring agent includes at least FD&C Blue #1 and FD&C Yellow #5.

22. The antimicrobial solution of claim 13, wherein said solution is a liquid denture cleanser.

23. The antimicrobial solution of claim 13, wherein said solution is a toothbrush cleanser.

24. The antimicrobial solution of claim 13, wherein said solution is a mouthwash.

25. The antimicrobial solution of claim 13, wherein said solution is a disinfectant.

26. An antimicrobial solution for topical and oral use consisting of:
   a) about 0.15% by weight of sodium lauryl sulfate as a cleansing agent;
   b) about 9.0% by weight of 50% hydrogen peroxide as an antibacterial agent;
   c) about 0.04% by weight of phosphoric acid as a reagent;
   d) about 90.81% by weight of water;
   e) FD&C Blue #1; and
   f) FD&C Yellow #5.

27. The antimicrobial solution of claim 25, wherein said solution is a denture cleanser.

28. The antimicrobial solution of claim 25, wherein said solution is a toothbrush cleanser.

29. The antimicrobial solution of claim 25, wherein said solution is a mouthwash.

30. The antimicrobial solution of claim 25, wherein said solution is a disinfectant.

* * * * *

UNITED STATES PATENT AND TRADEMARK OFFICE
CERTIFICATE OF CORRECTION

| | |
|---|---|
| PATENT NO. | : 7,094,430 B2 |
| APPLICATION NO. | : 10/610669 |
| DATED | : August 22, 2006 |
| INVENTOR(S) | : Grady F. Lawrence and W. Timothy Carlton |

It is certified that error appears in the above-identified patent and that said Letters Patent is hereby corrected as shown below:

Title Page, Item (55) & Col. 1, Lines 1-3

The title should read: ANTIMICROBIAL SOLUTION FOR BOTH TOPICAL AND ORAL USE

Claim 5, column 6, line 24, "4" should read --1--.

Claim 6, column 6, line 27, "4" should read --1--.

Claim 8, column 6, line 33, delete "is."

Claim 13, column 6, line 42, --and-- should be inserted between "topical" and "oral."

Claim 13, column 6, lines 48-49, delete "selected from the group consisting of FD&C blue#1 and FD&C Yellow #5".

Claim 19, column 6, line 67, insert --generally-- before "about."

Claim 26. column 7, line 17, insert --generally-- before "about."

Claim 26, column 8, line 1, insert --generally-- before "about."

Claim 26, column 8, line 3, insert --generally-- before "about."

Claim 26, column 8, line 4, insert --generally-- before "about."

Claim 27, column 8, line 8, "25" should read --26--.

Claim 28, column 8, line 10, "25" should read --26--.

Claim 29, column 8, line 12, "25" should read --26--.

UNITED STATES PATENT AND TRADEMARK OFFICE
CERTIFICATE OF CORRECTION

PATENT NO. : 7,094,430 B2
APPLICATION NO. : 10/610669
DATED : August 22, 2006
INVENTOR(S) : Grady F. Lawrence and W. Timothy Carlton It is certified that error appears in the above-identified patent and that said Letters Patent is hereby corrected as shown below:

Claim 30, column 8, line 14, "25" should read --26--.

Signed and Sealed this

Twenty-eighth Day of November, 2006

JON W. DUDAS
*Director of the United States Patent and Trademark Office*